US006660757B2

(12) United States Patent
Stutzmann et al.

(10) Patent No.: US 6,660,757 B2
(45) Date of Patent: Dec. 9, 2003

(54) USE OF RILUZOLE IN THE TREATING ACOUSTIC TRAUMAS

(75) Inventors: Jean-Marie Stutzmann, Villecresnes (FR); John Randle, Bookline, MA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/882,223

(22) Filed: Jun. 15, 2001

(65) Prior Publication Data

US 2002/0004516 A1 Jan. 10, 2002

Related U.S. Application Data

(63) Continuation of application No. PCT/FR99/03108, filed on Dec. 13, 1999.

(30) Foreign Application Priority Data

Dec. 15, 1998 (FR) .............................. 98 15834

(51) Int. Cl.[7] .............................. A61K 31/425
(52) U.S. Cl. .................. 514/367; 514/878; 514/879
(58) Field of Search ................. 514/367, 878, 514/879

(56) References Cited

U.S. PATENT DOCUMENTS 5,624,945 A    4/1997  Bousseau et al. ........... 514/367
5,716,961 A *  2/1998  Sands .......................... 514/277

FOREIGN PATENT DOCUMENTS

| EP | 50551   | 10/1981 |
| EP | 282971  | 3/1988  |
| EP | 305276  | 8/1988  |
| EP | 305277  | 8/1988  |
| WO | 9413288 | 6/1994  |
| WO | 9415600 | 7/1994  |
| WO | 9415601 | 7/1994  |
| WO | 9420103 | 9/1994  |
| WO | 9519170 | 7/1995  |

OTHER PUBLICATIONS

Abraham Shulman, M.D., *International Tinnitus Journal* vol. 3 (2), pp. 77–93 (1997).

Kretschmer, et al: *Naunyn–Schmiedeberg's Arch Pharmacol* vol. 358 (2), pp. 181–190 (1998).

Ehrenberger, et al: *Acta Otolaryngol* vol. 115, pp. 236–240 (1995).

* cited by examiner

*Primary Examiner*—Frederick Krass
(74) *Attorney, Agent, or Firm*—Balaram Gupta

(57) ABSTRACT

The invention concerns the use of riluzole or one of its pharmaceutically acceptable salts for preventing and/or treating acoustic traumas and, in particular, different types of deafness and tinnitus.

10 Claims, 2 Drawing Sheets

USE OF RILUZOLE IN THE TREATING ACOUSTIC TRAUMAS

This application is a continuation of International application No. PCT/FR99/03108, filed Dec. 13, 1999; which claims the benefit of priority of French Patent Application No. 98/15,834, filed Dec. 15, 1998.

The present invention relates to the use of riluzole or one of its pharmaceutically acceptable salts in the prevention and/or treatment of acoustic traumas and, in particular, of deafness and of tinnitus.

Riluzole (2-amino-6-trifluoromethoxy-benzothiazole) is marketed for the treatment of amyotrophic lateral sclerosis. This compound is also useful as an anticonvulsant, an anxiolytic and a hypnotic (EP 50551), in the treatment of schizophrenia (EP 305276), in the treatment of sleep disorders and of depression (EP 305277), in the treatment of cerebrovascular disorders and as an anesthetic (EP 282971), in the treatment of spinal, cranial and craniospinal traumas (WO 94/13288), as a radio restorative (WO 94/15600), in the treatment of Parkinson's disease (WO 94/15601), in the treatment of neuro-AIDS (WO 94/20103), in the treatment of mitochondrial diseases (WO 95/19170). All of these references are herein incorporated by reference in their entirety.

It has now been found that riluzole or one of its pharmaceutically acceptable salts can also be used in the prevention and/or treatment of acoustic traumas and, especially, of tinnitus and of deafness and, in particular, of deafness caused by sound traumas and age-related deafness.

Figure 1A:
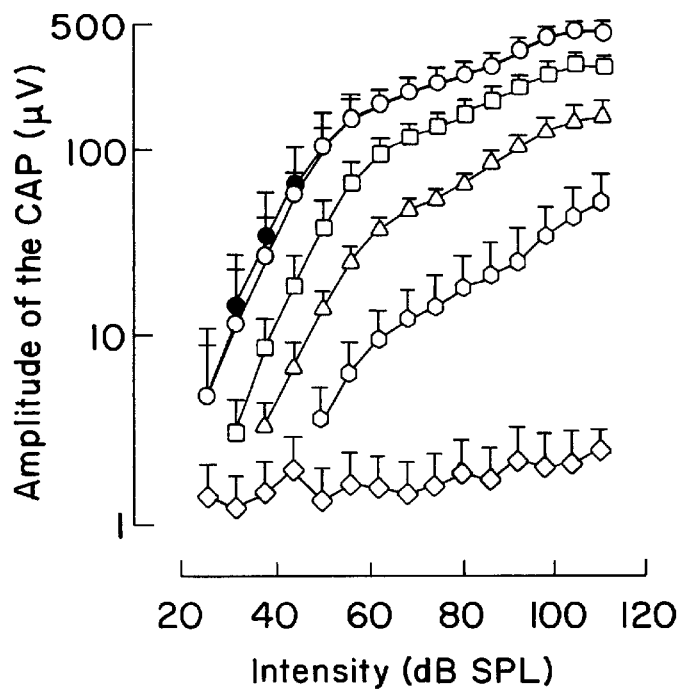
FIGS. 1a and 1b illustrate the effect of various dosage levels of riluzole on the amplitude of the compound action potential (CAP).

The organ of Corti in mammals possesses 2 types of cells: the inner ciliated cells (ICC) and the outer ciliated cells (OCC). The OCCs amplify the vibrations of the basilar membrane. The ICCs, the true sensory cells, convert this mechanical vibration to a message which can be interpreted by the central nervous system.

The evaluation of the functional state of the cochleae in guinea pigs which have been subjected to intense sound overstimulation (6 kHz, 130 dB SPL for 15 minutes) shows very high auditory losses (of the order of 80 dB). A histological evaluation of cochleae removed immediately after acoustic trauma shows not only mechanical damage to the ciliated cells but also bursting of the dendrites of the primary auditory neurons under the ICCs.

The effect of riluzole in increasing doses was studied according to the technique of acute perifusion of the cochleae:

10 tricolor guinea pigs weighing 200 to 400 g are anesthetized by intraperitoneal injection of urethane (1.4 g/kg) and then trachetomized and artificially ventilated. The external auditory canals are incised for the putting in place of ear bars in a restraining apparatus. During the entire duration of the experiment, the electrocardiogram is monitored and the central temperature regulated by means of a heating cover at 38.5±1° C. The experiments are carried out in a soundproofed, anechoic and faradized chamber. Access to the cochlea is obtained via a ventral approach. After opening of the tympanic bulla, 3 holes 0.2 mm in diameter are manually cut in the basal turn of the cochlea: the first in the tympanic ramp to receive an infusion pipette, the second in the vestibular ramp to allow the outflow of the infused solutions out of the cochlea and the third also in the vestibular ramp to receive a recording electrode.

The cochlear potentials recorded in the vestibular ramp are stored and then numerically filtered to dissociate the compound action potential (CAP), a control for the activity of the auditory nerve and the receptor potentials obtained from the ciliated cells, namely the microphonic potential (MP) and the summation potential (SP). A low-pass filter of 2.5 kHz is used to extract the CAP whose amplitude is measured between N1 (1st negative wave) and P1 (1st positive wave) as well as the SP measured between 0 and 5 ms. A band-pass filter around 8 kHz (acoustic stimulation frequency) is used to extract the MP (6–10 kHz, filter slope: 48 db/octave).

After introducing the pipette (about 0.1 mm in diameter at the tip) into the tympanic ramp with the aid of a micromanipulator, leaktightness being provided by means of a glue ball placed near the tip, artificial perilymph is infused at the rate of 2.5 $\mu$l/min. A second infusion of artificial perilymph containing 0.1% dimethyl sulfoxide is carried out. If this second infusion does not modify the cochlear potentials, this perilymph serves as vehicle for studying the effect of increasing doses of riluzole on the cochlear potentials. These cochlear potentials are recorded immediately after each infusion. The duration of the infusions is 10 minutes.

Figure 1B:
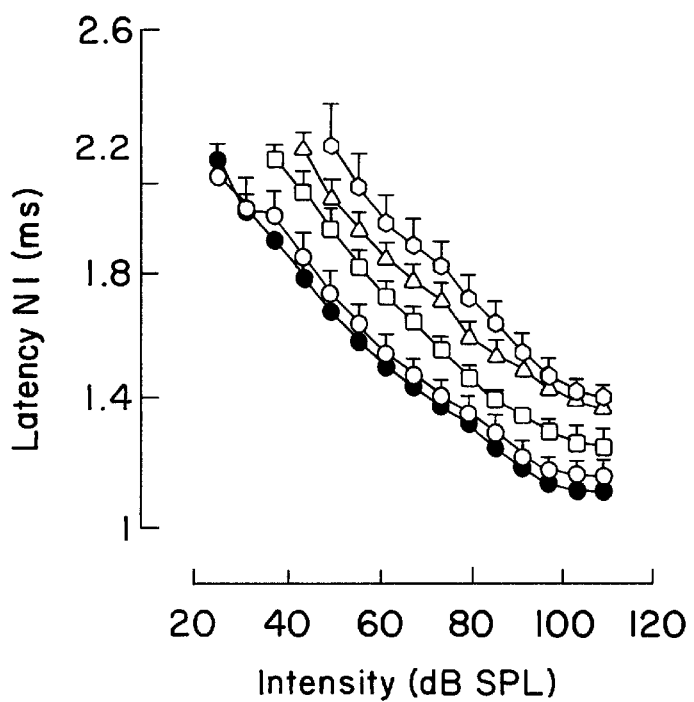
Figure 2:
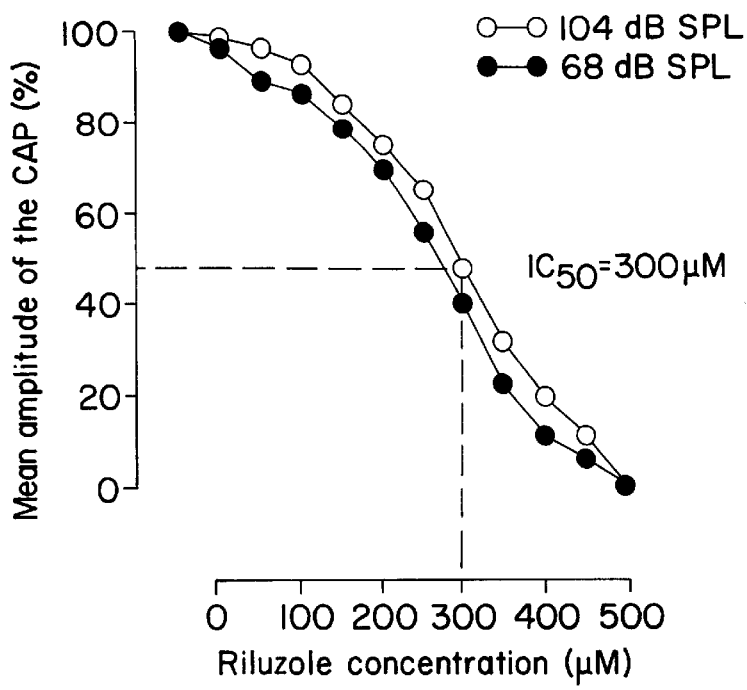
FIG. 2 is a graph illustrating the relationship between mean amplitude of the CAP and the riluzole concentration.

The infusion of cumulative and increasing doses of riluzole (50 to 500 $\mu$M) diluted in the same perilymph containing dimethyl sulfoxide (0.1%) causes a reduction in the compound action potential (CAP) of the auditory nerve dependant on the dose applied in the cochlea and an increase in the latency N1 of this potential (FIGS. 1a and 1b, filled circles: the perilymph alone, open circles: perilymph+ dimethyl sulfoxide, squares: perilymph containing 250 $\mu$M riluzole, triangles: perilymph containing 350 $\mu$M riluzole, hexagons: perilymph containing 450 $\mu$M riluzole and diamonds: perilymph containing 500 $\mu$M riluzole). The IC50 is observed for a dose of 300 $\mu$M (FIG. 2). In all the animals, a complete disappearance of the CAP is obtained for a dose of 500 $\mu$M.

The protective effect on acoustic trauma was tested on 10 animals for which a preliminary infusion of artificial perilymph is carried out for 10 minutes. After evaluation of the audiometric thresholds, a second 35 minute infusion either of artificial perilymph alone (5 animals: control group) or of perilymph containing 500 $\mu$M riluzole (5 animals) is carried out. Ten minutes after the start of the second infusion, a sound overstimulation (6 kHz, 130 dB SPL) is applied for 15 minutes. Finally, a third infusion of artificial perilymph allows rinsing of the cochlea. The audiometric thresholds are then recorded. The auditory loss for each frequency induced by sound exposure is defined as the difference between the audiometric thresholds recorded before and after the sound over-exposure.

Figure 3:
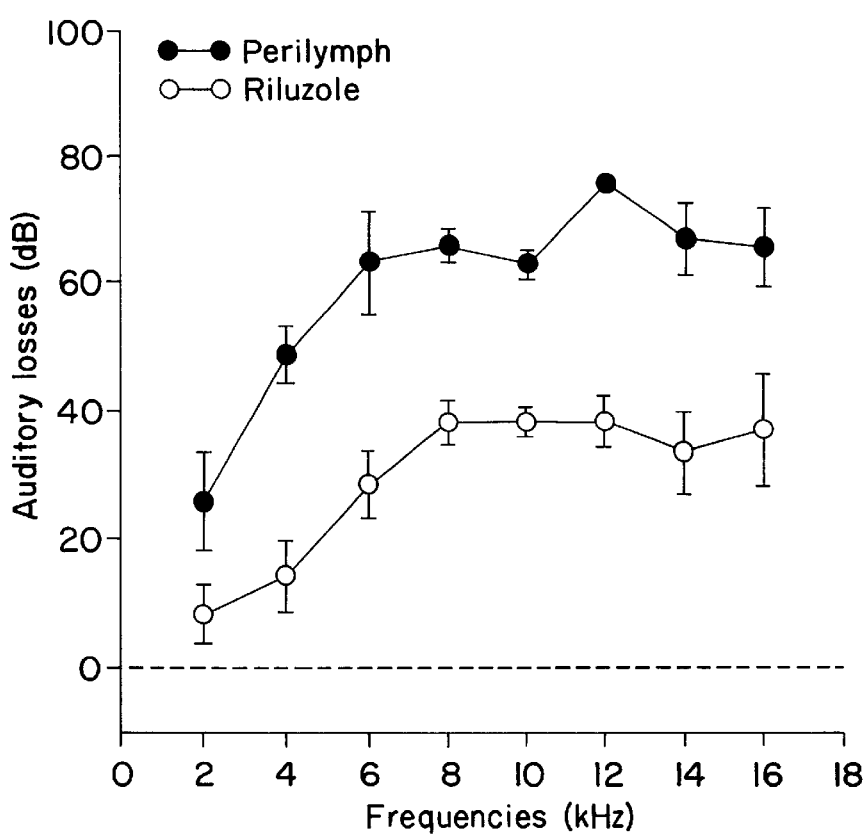
FIG. 3 is a graph illustrating the relationship between auditory losses at various frequencies.

The control group exhibits, for frequencies of between 8 and 16 kHz, much higher auditory losses than the group treated with 500 $\mu$M riluzole (FIG. 3, filled circles: perilymph alone, open circles: perilymph containing 500 $\mu$M riluzole).

Histological study of the cochleae by electron microscopy shows, in the control group, complete destruction of the endings of the auditory nerve fibers and in the group treated with riluzole, a virtually normal innervation.

As pharmaceutically acceptable salts of riluzole, there may be mentioned especially the addition salts with inorganic acids such as hydrochloride, sulfate, nitrate, phosphate, or organic acids such as acetate, propionate, succinate, oxalate, benzoate, fumarate, maleate, methanesulfonate, isethionate, theophyllineacetate, salicylate, phenolphthalinate, methylene-bis-β-oxy-naphthoate or substitution derivatives of these derivatives.

The medicaments consist of at least riluzole in free form or in the form of an addition salt with a pharmaceutically acceptable acid, in a pure state or in the form of a composition in which it is combined with any other pharmaceutically compatible product, which may be inert or physiologically active. The medicaments according to the invention may be used by the oral, parenteral, rectal or topical route.

As solid compositions for oral administration, tablets, pills, powders, (gelatin capsules, cachets) or granules may be used. In these compositions the active ingredient according to the invention is mixed with one or more inert diluents such as starch, cellulose, sucrose, lactose or silica, under an argon stream. These compositions may also comprise substances other than diluents, for example one or more lubricants such as magnesium stearate or talc, a coloring, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The sterile compositions for parenteral administration may preferably be solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be carried out in several ways, for example by aseptisizing filtration, by incorporating sterilizing agents into the composition, by irradiation or by heating. They can also be prepared in the form of sterile solid compositions which can be dissolved at the time of use in sterile water or in any other injectable sterile medium.

The compositions for rectal administration are suppositories or rectal capsules which contain, in addition to the active product, excipients such as cocoa butter, semisynthetic glycerides or polyethylene glycols.

The compositions for topical administration may be, for example, creams, lotions, collyria, mouthwash, nasal drops or aerosols.

The doses depend on the desired effect, the duration of the treatment and the route of administration used; they are generally between 50 and 400 mg per day by the oral route for an adult with unit doses ranging from 25 to 200 mg of active substance.

In general, the doctor will determine the appropriate dosage according to the age, weight and all the other factors specific to the subject to be treated.

The following examples illustrate medicaments according to the invention:

EXAMPLE A

Tablets containing a 50 mg dose of active product having the following composition are prepared according to the usual technique:

| | |
|---|---|
| Riluzole | 50 mg |
| Mannitol | 64 mg |

-continued

| | |
|---|---|
| Microcrystalline cellulose | 50 mg |
| Polyvidone excipient | 12 mg |
| Sodium carboxymethylstarch | 16 mg |
| Talc | 4 mg |
| Magnesium stearate | 2 mg |
| Anhydrous colloidal silica | 2 mg |
| Mixture of methylhydroxypropylcellulose, polyethylene glycol 6000, titanium dioxide (72-3.5-24.5) | 245 mg |
| qs 1 finished film-coated tablet weighing | |

EXAMPLE B

Gelatin capsules containing a 50 mg dose of active product having the following composition are prepared according to the usual technique:

| | |
|---|---|
| Riluzole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injectable solution containing 10 mg of active product having the following composition is prepared:

| | |
|---|---|
| Riluzole | 10 mg |
| Benzoic acid | 80 mg |
| Benzyl alcohol | 0.06 cm$^3$ |
| Sodium benzoate | 80 mg |
| Ethanol at 95% | 0.4 cm$^3$ |
| Sodium hydroxide | 24 mg |
| Propylene glycol | 1.6 cm$^3$ |
| Water    qs | 4 cm$^3$ |

What is claimed is:

1. A method of treating acoustic trauma comprising administering to a patient in need of said treatment a therapeutically effective amount of riluzole or one of its pharmaceutically acceptable salts.

2. The method according to claim 1, wherein the acoustic trauma is tinnitus.

3. The method according to claim 1, wherein the acoustic trauma is deafness.

4. The method according to claim 3, wherein the deafness is caused by sound trauma.

5. The method according to claim 3, wherein the deafness is age-related.

6. The method according to claim 1, wherein riluzole is administered at a dosage level of from about 25 to about 200 mg.

7. The method according to claim 2, wherein riluzole is administered at a dosage level of from about 25 to about 200 mg.

8. The method according to claim 3, wherein riluzole is administered at a dosage level of from about 25 to about 200 mg.

9. The method according to claim 4, wherein riluzole is administered at a dosage level of from about 25 to about 200 mg.

10. The method according to claim 5, wherein riluzole is administered at a dosage level of 25 to 200 mg.

* * * * *